United States Patent [19]
Duprat

[11] Patent Number: 6,045,563
[45] Date of Patent: Apr. 4, 2000

[54] ARTIFICIAL CHAMBER FOR EXTRACTING A CORNEAL GRAFT

[75] Inventor: Alain Duprat, Roquettes, France

[73] Assignee: Moria SA, Antony, France

[21] Appl. No.: 09/328,366

[22] Filed: Jun. 9, 1999

[30] Foreign Application Priority Data

Jun. 19, 1998 [FR] France ................................. 98 07775

[51] Int. Cl.⁷ ................................................. A61B 17/00
[52] U.S. Cl. ........................................................... 606/166
[58] Field of Search .................................. 606/166, 167, 606/1, 172, 180; 623/4–6; 206/363, 370; 215/276

[56] References Cited

U.S. PATENT DOCUMENTS

| | | |
|---|---|---|
| 4,738,401 | 4/1988 | Filicicchia . |
| 4,865,033 | 9/1989 | Krumeich et al. . |
| 4,884,570 | 12/1989 | Krumeich et al. . |
| 4,982,969 | 1/1991 | Sukhareva et al. . |
| 5,108,412 | 4/1992 | Krumeich et al. ...................... 606/166 |

FOREIGN PATENT DOCUMENTS 2712184  5/1995  France .

OTHER PUBLICATIONS

Database WPI Section PQ, Week 9422 Derwent Publications Ltd. London GB, Class P32, AN 94–181063 XP002095602 & SU 1 801 422 A (VLOG MED INST).

Primary Examiner—Gary Jackson
Assistant Examiner—William Lewis
Attorney, Agent, or Firm—Griffin, Butler, Whisenhunt & Szipl, LLP

[57] ABSTRACT

An artificial chamber for a corneo-scleral disk for the purpose of taking a graft therefrom, the chamber comprising a stand, a cornea support carried by the stand, having a vertical axis, and possessing a head having a supporting top face into which there opens out at least one feed orifice, and a clamping ring for clamping the corneo-scleral disk on the cornea support. The clamping ring is fixed and carried by the stand, while the cornea support is mounted on the stand so as to slide along the vertical axis of the cornea support under drive from actuator means.

10 Claims, 2 Drawing Sheets

FIG_1

ARTIFICIAL CHAMBER FOR EXTRACTING A CORNEAL GRAFT

The present invention relates to an artificial chamber for receiving a corneo-scleral disk taken from a donor to enable a graft to be taken from its epithelial face.

BACKGROUND OF THE INVENTION

Over the last few years, progress has been achieved in developing liquids for conserving corneas that have been taken for use as grafts. At present, the disk comprising the cornea surrounded by a scleral ring having a width of one or two millimeters is put in a conservation liquid and can be used a few days later.

The graft proper is cut to shape by means of an assembly known as an artificial chamber which holds the cornea by clamping it via the scleral ring and which has means for supporting a cutting tool known as a keratome. Two types of keratome are available: a bore or a plane, depending on whether the operator desires to make a perforating cut (i.e. through the entire thickness of the cornea), or on the contrary a lamellar cut comprising a determined thickness of the cornea. The artificial chamber serves to stiffen the cornea by pressurizing it using physiological serum or air, thus making it possible to perform cutting via the front face (epithelium) under conditions that are very close to those that exist when removing diseased cornea that needs to be replaced.

Various structures have already been proposed for artificial chambers. In particular, French patent No. 2 712 184 discloses an artificial chamber comprising a stand, a cornea support carried by the stand, having a vertical axis and possessing a head with a supporting top face into which there opens up at least one feed orifice, and a clamping ring that is movable in translation relative to the cornea support along the axis thereof between a clamping position in which its top face clamps the corneo-scleral disk against the clamping ring, and a release position in which its top face is at a distance from the clamping ring.

OBJECTS AND SUMMARY OF THE INVENTION

An object of the invention is to propose an ergonomic artificial chamber system that makes handling, disassembly, and sterilization easy, while nevertheless being simple to manufacture and of low cost.

The invention provides an artificial chamber for a corneoscleral disk for the purpose of taking a graft therefrom, the chamber comprising a stand, a cornea support carried by the stand, having a vertical axis, and possessing a head having a supporting top face into which there opens out at least one feed orifice, and a clamping ring for clamping the corneoscleral disk on the cornea support, in which the clamping ring is fixed and carried by the stand, while the cornea support is mounted on the stand so as to slide along the vertical axis of the cornea support under drive from actuator means.

In a first embodiment, the actuator means of the cornea support are constituted by a screw-and-nut system, the cornea support possessing a screw-forming threaded portion which is prevented from rotating relative to the stand and which co-operates with a nut mounted on the stand to rotate freely without moving in translation along the axis of the cornea support.

In an improved, second embodiment, the actuator means of the cornea support are constituted by a double-acting actuator. The surgeon or an assistant can then control displacement of the cornea support in a manner that is convenient and precise. In particular, the actuator can be driven by means of an appropriate drive member such as a pedal which leaves the surgeon's hands free.

According to an advantageous characteristic of the invention, the clamping ring is removably mounted on the stand.

In which case, it is advantageous for the releasable fixing of the clamping ring on the stand to be provided by means of a bayonet system.

Also advantageously, when the actuator system for the cornea support is made in the form of a screw-and-nut system, the clamping ring is connected to the stand by means of a link portion which surrounds the actuator nut of the cornea support and which is perforated so as to allow the nut to be actuated by hand.

According to another advantageous characteristic of the invention, the clamping ring is carried by the top edge of a collar which covers the head of the cornea support.

The collar has an outside thread on which a nut is engaged which forms a stop of adjustable height for a keratotomy accessory that covers the clamping collar.

It is then advantageous to make provision for the collar to have an outside thread on which a nut is engaged that forms an abutment of adjustable height for a keratotomy accessory that covers the clamping collar.

Advantageously, under such circumstances, the keratotomy accessory is fitted with a member for locking it to the clamping collar.

BRIEF DESCRIPTION OF THE DRAWINGS

Other characteristics and advantages of the invention appear on reading the following description of particular embodiments given as non-limiting examples.

Reference is made to the accompanying drawings, in which.

MORE DETAILED DESCRIPTION

Figure 1:
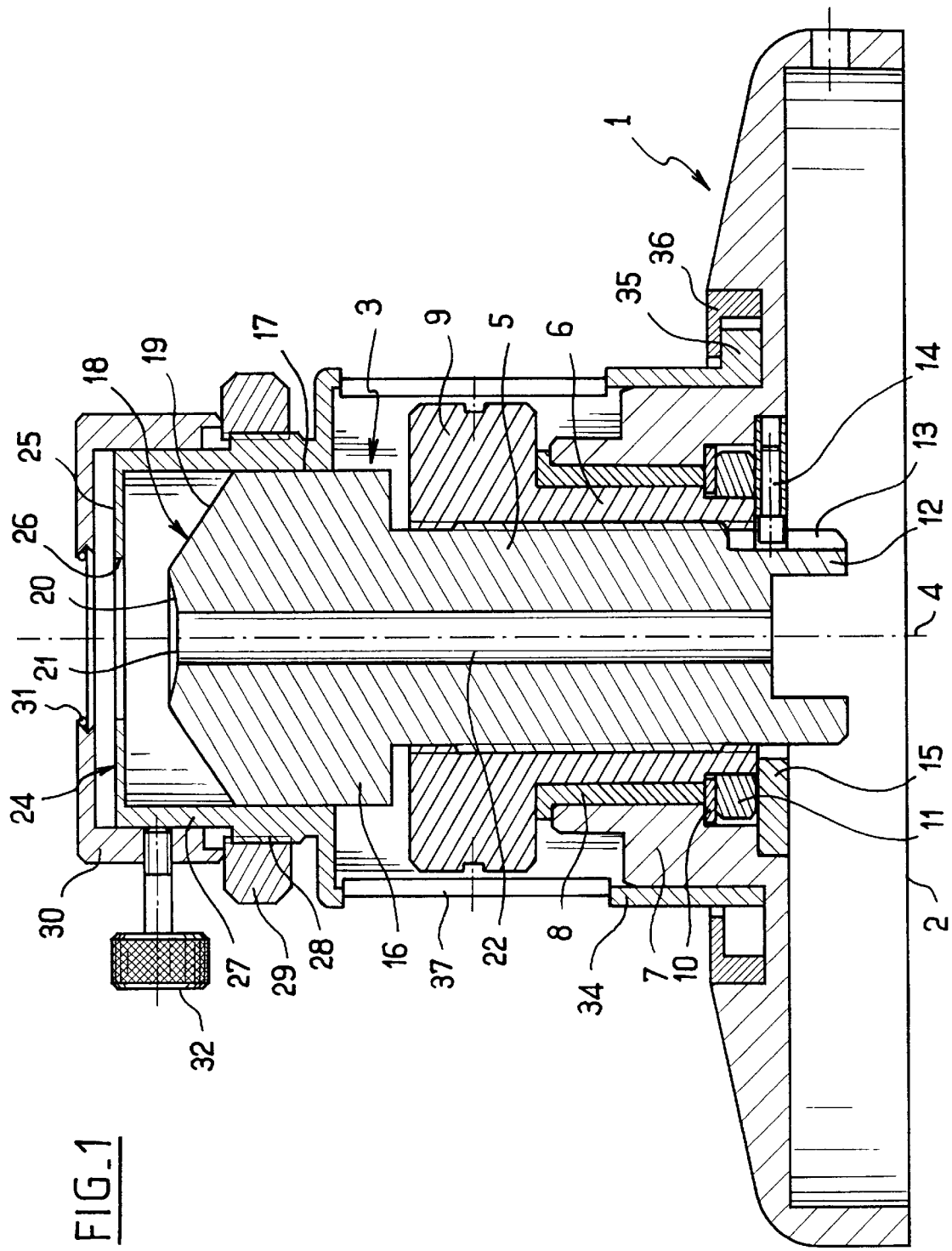
FIG. 1 is an axial view of an artificial chamber constituting a first embodiment of the invention.

With reference to FIG. 1, an artificial chamber of the invention comprises a stand, generally 1 having a plane bottom face 2 that is substantially horizontal.

A cornea support generally 3 in the form of a stepped cylinder about a vertical axis 4 is mounted on the stand 1 to slide along its vertical axis 4. The sliding mount of the cornea support 3 on the stand 1 and control thereof are provided by means of a screw-and-nut system. The cornea support 3 thus has a threaded middle portion 5 whose outside thread co-operates with a nut 6 mounted to rotate freely on the stand 1 but without moving in translation along the axis 4.

More precisely, the stand 1 has a bearing surface 7 about the axis 4 which is fitted with a bushing 8 in which the nut 6 is received so as to rotate freely. The nut is prevented from moving axially by abutments associated with the nut and with the bushing 8. Specifically, at its top end, the nut 6 has an enlarged annular portion 9 which enables the nut 6 to be rotated manually and which also comes into abutment against the top end of the bushing 8. At its bottom end, the nut 6 is fitted with a stop washer 10 locked against a shoulder of the nut 6 by a lock nut 11.

To prevent the cornea support 3 being rotated by the nut 6, the cornea support 3 is indexed to the stand 1. To this end, the cornea support 3 is provided at its bottom end 12 with a groove 13 parallel to the axis 4 and in which there is received an indexing peg 14 which is housed in an insert 15 in the form of a washer fitted to the stand 1 at the bottom end of the bearing surface 7.

At its top portion, the cornea support 3 has a head 16 which is substantially larger than its threaded portion 5. This head 16 has a cylindrical side face 17 and a top support face, generally 18. The top face 18 comprises two portions: a frustoconical peripheral portion 19 and a concave central portion 20 centered on the axis 4 and into which there opens out a feed orifice 21 formed by the top end of a feed channel 22 passing right through the cornea support 3 along the axis 4.

A clamping cap, generally 24 which is fixed and carried by the stand 1 is disposed over the top face 18 of the cornea support 3 so as to clamp the periphery of the corneo-scleral disk when it is in place on the top face 18 of the cornea support 3 and the cornea support 3 is raised into the clamping position.

More precisely, the clamping cap 24 possesses a clamping ring 25 in the form of a disk having a hollowed-out center presenting a circularly-shaped inside edge 26 centered on the axis 4. The diameter of the edge 26 is slightly greater than the diameter of the concave central portion 20 of the top face 18 of the cornea support 3 so that in the clamping position, the inside edge 26 of the clamping ring 25 comes to "bite" against the periphery of the corneo-scleral disk around the concave central portion 20 of the support face 18.

The clamping cap 24 also possesses, beneath the clamping ring 25, a centering portion 27 in the form of a cylindrical collar whose inside face matches the cylindrical side face 17 of the head 16 of the cornea support 3. This collar (centering portion) 27 is fitted over the head 16 of the cornea support 3 to improve centering of the clamping ring 25 relative to the axis 4 of the cornea support 3.

In addition, the collar 27 has an outside thread 28 on which there is engaged a nut 29 forming a stop that is of adjustable height for a keratotomy accessory 30 in the form of a cap that fits over the clamping cap 24. In this case, the keratotomy accessory 30 is a support for guiding a keratome having dove tail-shaped grooves 31. However, prior to the keratotomy operation itself, it is also possible to place on the clamping cap 24 an accessory that is similar to a transparent cup that serves to measure the diameter of the graft that is to be cut out.

In the example shown, the accessory 30 is fitted with a transverse locking screw 32 which can be clamped against the outside face of the collar 27 to lock the position of the keratotomy accessory 30.

The bottom edge of the collar 37 is connected to the stand 1 via a link portion 34 which surrounds the drive nut 6 and the bearing surface 7 and which is provided at its bottom end with a flange 35 which co-operates with a complementary flange 36 associated with the stand 1 to form a bayonet system for releasably securing the cap 24 to the stand 1.

This link portion 34 has perforations in the form of through openings giving direct access to the annular drive portion 9 of the nut 6 so as to make it easy to handle.

The above-described artificial chamber is used as follows. The clamping cap 24 is released from the cornea support 3 so as to give direct access to the top face 18 thereof, and a corneo-scleral disk is placed on the center of the face 18, covering the concave central portion 20 and projecting in part over the frustoconical peripheral portion 19. The clamping cap 24 is put back into place so as to cover the head 16 of the cornea support 3 in part. The flange 35 is engaged in appropriate manner beneath the flange 36 and the clamping cap 24 is rotated through a fraction of a turn (e.g. one-fourth of a turn) for quick and reliable locking relative to the stand 1.

With the cornea support 3 initially being in its low or release position, i.e. in a position where its top face 18 is at a distance from the clamping ring 25, the nut 6 is rotated via its handling annular portion 9 so as to cause the cornea support 3 to move upwards in translation until it comes into the clamping position with its top face 18 against the edge 26 of the clamping ring 25. The periphery of the corneo-scleral disk is then clamped between the edge 26 and the frustoconical portion 19 of the top face 18 of the cornea support 3. The clamping force can be adjusted by tightening the nut 9 at the end of its stroke to a greater or lesser extent.

The sealed volume which is then formed between the corneo-scleral disk and the concave central portion 20 of the top face 18 of the cornea support constitutes the artificial chamber proper. The feed channel 22 is connected to a pneumatic or hydraulic feed device so that the artificial chamber is put under pressure, thereby simulating the internal pressure of the eye and causing the corneo-scleral disk to take up its natural convex shape. The corneo-scleral disk once shaped in this way by the pressurization projects above the clamping ring 25 and is thus properly positioned for keratotomy.

The relative positioning of the keratome (only the guiding support 30 thereof being shown in FIG. 1) can then be adjusted by modifying the position of the stop nut 29. This adjustment in height determines the extent to which the corneo-scleral disk is flattened during keratotomy, and thus the diameter of the graft taking therefrom. The locking screw 32 serves to hold the accessory 30 in place once its position has been adjusted.

Figure 2:
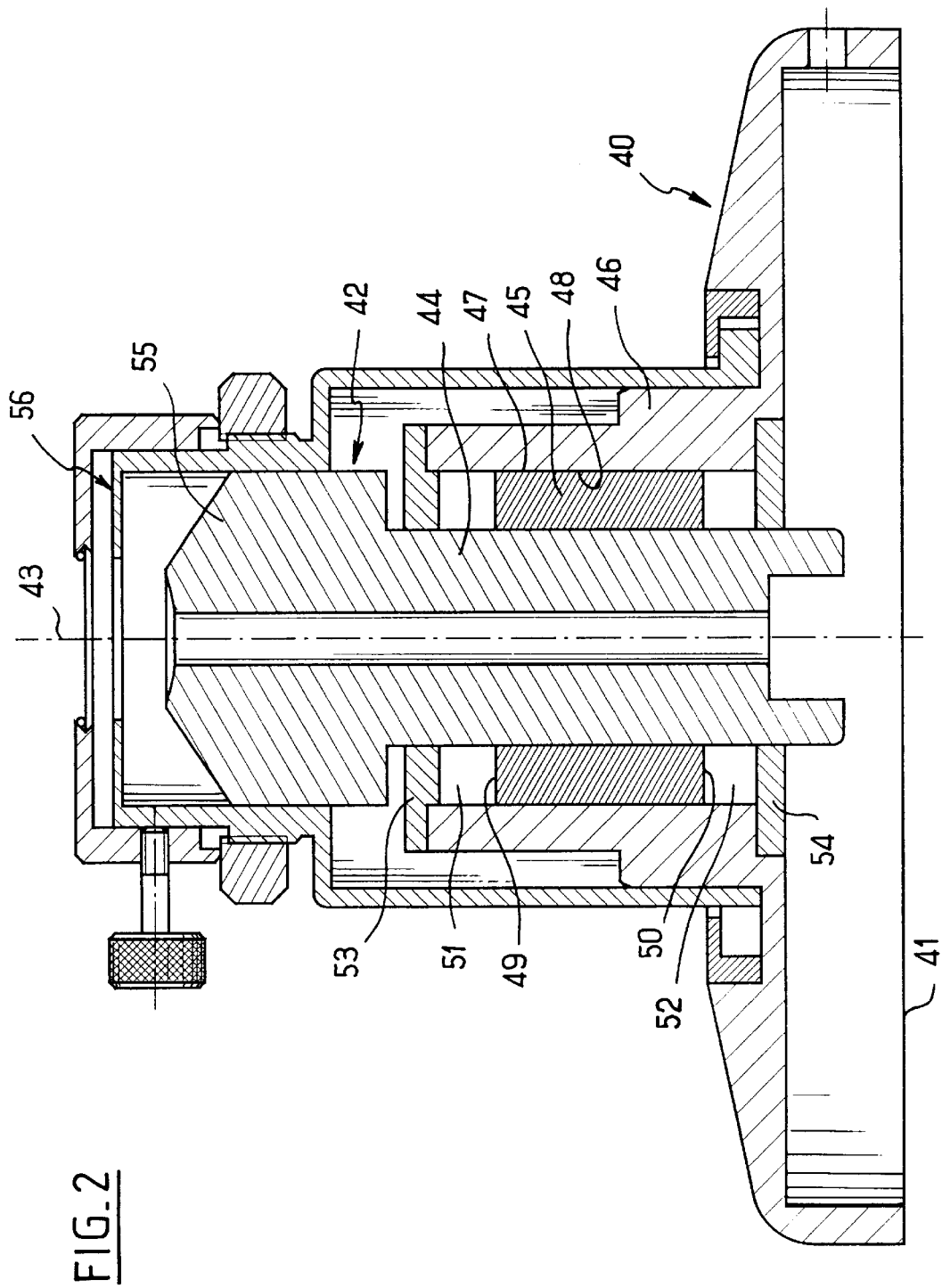
FIG. 2 is a view analogous to FIG. 1 showing a second embodiment of the invention.

FIG. 2 shows a second embodiment of an artificial chamber of the invention.

Like the preceding chamber, this chamber comprises a stand 40 having a plane bottom face 41 that is substantially horizontal.

A cornea support 42 in the form of a stepped cylinder about a vertical axis 43 is mounted on the stand 40 to slide along its vertical axis 43. Unlike the embodiment described above, the sliding mount of the cornea support 42 on the stand 1, and control thereof are provided by means of a double-acting actuator system that may be pneumatic or hydraulic. The cornea support 42 thus has a bottom portion 44 which constitutes the rod of an actuator whose body is formed by a cylindrical sheath 46 about the axis 43 and received in the stand 40. More precisely, the rod (bottom portion) 44 is provided with a shoulder 45 that has a side face 47 that is slidably received in the sheath 46 whose cylindrical inside face 48 is of substantially the same diameter. The shoulder 45 may optionally be provided with a gasket so as to improve sealing relative to the sheath 46. Two end plates 53 and 54 carried on the top and bottom ends of the sheath 46 serve to close the sheath 46 a in sealed manner relative to the top and bottom portions of the rod 44 on either side of the shoulder 45. The shoulder has two active radial faces, a top face 49 and a bottom face 50 which co-operate with the sheath 46, the end plates 53 and 54, and the rod 44 to define top and bottom chambers 51 and 52 which can be fed with gas or liquid by a conventional type of control and feed circuit (not shown in the figures).

Thus, the cornea support 42 is raised towards its clamping position by putting the bottom chamber 52 under pressure. Conversely, the cornea support 42 is lowered towards its release position by putting the top chamber 51 under pressure. The actuator system can be controlled by means of a pedal control member which has the advantage of leaving the operator's hands free. In addition, the use of an actuator system offers the advantage of enabling the clamping force exerted by the cornea support 42 against the clamping collar to be adjusted in convenient and accurate manner, which is sometimes necessary in order to obtain optimum clamping without damaging the corneo-scleral disk.

At its top end, the cornea support 42 possesses a head 55 which is identical to the head 16 of the embodiment described above with reference to FIG. 1. Similarly, the artificial chamber has a clamping cap 56 which is practically identical to the clamping cap 24 of the embodiment described above with reference to FIG. 1. The only difference in the clamping cap compared with that described above lies in the absence of the opening provided in its portion connecting it to the stand 40, since such openings are now pointless given that the operator does not act directly on the system for actuating the cornea support.

The invention is not limited to the embodiments described above, but on the contrary covers any variant using equivalent means to reproduce the essential characteristics of the invention.

What is claimed is:

1. An artificial chamber for removal of a graft from a corneo-scleral disk, comprising:

(1) a stand;

(2) a corneo support mounted on the stand such as to be slideable on the stand along a vertical axis of the corneo support by means of a drive actuator, said corneo support having a head, a supporting top face on the head and at least one feed orifice opening into the top face for supplying a fluid thereto; and (3) a clamping ring fixable to and carried by the stand such that the corneo-scleral disk is clampable by the clamping ring to the corneo support.

2. An artificial chamber according to claim 1, wherein the actuator of the cornea support is constituted by a screw-and-nut system, the cornea support having a screw-forming threaded portion which is prevented from rotating relative to the stand and which co-operates with a nut mounted on the stand to rotate freely without moving in translation along the vertical axis of the cornea support.

3. An artificial chamber according to claim 1, wherein the actuator of the cornea support is constituted by a double-acting actuator.

4. An artificial chamber according to claim 3, wherein the cornea support has a bottom portion which constitutes a rod of the actuator.

5. An artificial chamber according to claim 1, wherein the clamping ring is removably mounted on the stand.

6. An artificial chamber according to claim 5, wherein the removable mounting of the clamping ring on the stand is provided by means of a bayonet system.

7. An artificial chamber according to claim 2, wherein the clamping ring is removably mounted on the stand by means of a link portion which surrounds the nut of the cornea support and which is perforated so as to allow the nut to be actuated by hand.

8. An artificial chamber according to claim 1, wherein the clamping ring is carried by a top edge of a collar which covers the head of the cornea support.

9. An artificial chamber according to claim 8, wherein the collar has an outside thread on which a nut is engaged so as to form a stop of adjustable height for a keratotomy accessory that covers the clamping collar.

10. An artificial chamber according to claim 9, wherein the keratotomy accessory is fitted with a member for locking it to the clamping collar.

* * * * *